United States Patent
Suzuki et al.

(10) Patent No.: US 6,828,568 B2
(45) Date of Patent: Dec. 7, 2004

(54) PROCESS FOR TESTING OF FLUOPHORS AND DEVICE FOR CARRYING OUT THE PROCESS

(75) Inventors: Shinji Suzuki, Kanagawa-ken (JP); Sayu Yamada, Kanagawa-ken (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 37 days.

(21) Appl. No.: 10/274,992

(22) Filed: Oct. 22, 2002

(65) Prior Publication Data
US 2003/0075687 A1 Apr. 24, 2003

(30) Foreign Application Priority Data
Oct. 22, 2001 (JP) ........................................ 2001-323399

(51) Int. Cl.[7] .............................................. G06K 9/00
(52) U.S. Cl. .................................. 250/458.1; 250/459.1
(58) Field of Search ........................... 250/458.1, 459.1, 250/491.1, 492.2, 492.21, 492.22, 492.23, 498.1, 306, 366, 492.1; 382/128, 133; 435/6; 313/570

(56) References Cited

U.S. PATENT DOCUMENTS

| | | | |
|---|---|---|---|
| 5,471,278 A | | 11/1995 | Yasuda et al. |
| 5,479,024 A | * | 12/1995 | Hillner et al. ............ 250/458.1 |
| 5,481,159 A | | 1/1996 | Hiramoto et al. |
| 5,541,481 A | | 7/1996 | Yamaguchi et al. |
| 5,739,636 A | | 4/1998 | Yamaguchi et al. |
| 6,084,360 A | * | 7/2000 | Yokokawa et al. ......... 315/287 |
| 6,342,702 B1 | * | 1/2002 | Jinbo et al. ............... 250/492.1 |
| 6,345,115 B1 | * | 2/2002 | Ramm et al. ................ 382/133 |
| 6,372,895 B1 | * | 4/2002 | Bentsen et al. .............. 536/4.1 |
| 6,373,965 B1 | * | 4/2002 | Liang ........................ 382/112 |
| 6,508,990 B1 | * | 1/2003 | Yoshida et al. ......... 422/186.05 |
| 6,566,508 B2 | * | 5/2003 | Bentsen et al. .............. 536/4.1 |
| 6,654,119 B1 | * | 11/2003 | Gould et al. ................ 356/318 |

FOREIGN PATENT DOCUMENTS

| JP | 7050153 | 2/1995 |
|---|---|---|
| JP | 3171004 | 10/1995 |

\* cited by examiner

*Primary Examiner*—Constantine Hannaher
*Assistant Examiner*—Otilia Gabor
(74) *Attorney, Agent, or Firm*—Nixon Peabody LLP; David S. Safran

(57) ABSTRACT

A method and apparatus for increasing the emission amount of red such that it is made the same as the emission amount of green and blue, to enable the application state of the fluophors to be easily tested within a short time. Light from a discharge lamp of the short-arc type in which the arc tube is filled with cadmium and rare gas and which has emission lines between 200 nm and 230 nm is radiated onto fluophors of a test article such as the substrate for a display. The fluorescence produced by these fluophors is received by a CCD sensor, and displayed in a display part, and thus the application state, such as faults of the fluophors or the like, is checked. The images picked up by the CCD camera can also be input to a control device and thus testing can be automated. Furthermore, the lamp can be a dielectric barrier discharge excimer lamp which has electrodes for carrying out a dielectric barrier discharge and a discharge vessel which is filled with krypton gas and chlorine gas, and which has emission wavelengths between 200 nm and 230 nm.

6 Claims, 8 Drawing Sheets

PROCESS FOR TESTING OF FLUOPHORS AND DEVICE FOR CARRYING OUT THE PROCESS

BACKGROUND OF THE INVENTION

1. Field of the Invention

The invention relates to a process for testing fluophors and a device for carrying out the process. The invention relates especially to a process for testing fluophors which can be used for testing a substrate for image display, such as a PDP (plasma display panel), FED (field emission display) or the like, and a device for carrying out the process.

2. Description of the Prior Art

A red (R) fluophor, a green (G) fluophor and a blue (B) fluophor (hereinafter called only "R", "G", and "B") are applied to the above-described substrate for image display, such as PDP, FED or the like. By irradiation of the substrate with UV light or the like and by emission of these fluophors a color image is displayed.

If the above-described fluophors have faults or nonuniformities or when the above-described fluophors are mixed with fluophors with other colors, the expected characteristic cannot be obtained. In the production of the above-described substrate for image display, therefore, the state in which the above-described fluophors are applied is checked.

For example, testing of fluophors which are applied to a PDP are described below.

FIGS. 12(a) and 12(b) are each a schematic cross section of a PDP. A PDP has the arrangement shown in FIG. 12(a) in which on a rear substrate 101 (glass substrate: opaque) there are ribs 101a and in which thus pixels (cells) 102 are formed which are covered with transparent glass 103. Fluophors R, G and B are applied to the bottom (side of the rear substrate) and the sides (sides of the ribs) on the inside of the respective cell. Each cell 102 is filled with xenon gas. Above and below the cell one electrode 104a and an electrode 104b, respectively, are formed. By a discharge between these electrodes the xenon gas emits vacuum UV light (147 nm). The fluophors emit fluorescent radiation with the respective color, the emission of this xenon gas acting as the excitation radiation.

In the manufacturing process for PDP, after applying the fluophors R, G, and B to the respective cell on the substrate and before installation of the upper glass 103 in the manner shown in FIG. 12(b), it is checked whether the fluophors have been correctly applied to the respective pixel of the rear substrate 101.

The test has the checks for the following criteria: (1) Whether application to the required locations has taken place; (2) Whether there is any outswelling or fault; (3) Whether R, G, and B are not mixed on the boundary lines; and (3) Whether there is any nonuniformity of application, as shown, for example, in FIG. 13. Occasionally the following test criteria is herein generally referred to as "testing of the application state."

In order to test the state of application of the fluophors, the fluophors must be caused to emit. The reason for this is that the above-described fluophors which emit R, G, and B are white under visible radiation and that they cannot be distinguished from one another.

To cause the fluophors to emit, the fluophors are irradiated with excitation light. Conventionally, the light source of this excitation light is a super-high pressure mercury lamp or a xenon lamp. For the light from these lamps, however, the fluophors G and B emit fluorescent light in a sufficient amount, but the fluophor R hardly emits. Therefore, only an emission intensity of roughly $\frac{1}{10}$ to $\frac{1}{50}$ of the fluophors G and B was obtained. Therefore, mixing of R with other colors and outswelling could not be easily differentiated and the time consumption for the test was very high.

Further, since the amount of light of R is smaller than G or B there are cases in which the emission limit of the measurement device is not reached; this prevents automation of the test. For a xenon lamp, xenon gas is discharged and thus emission is carried out. But since the glass comprising the arc tube of the lamp does not transmit light with a wavelength of 147 nm, fluophors cannot be irradiated with light with a wavelength of 147 nm using a xenon lamp.

The emission of R is dark because the energy required for excitation of the fluophor R is greater than the energy required for excitation of the fluophor B or G. With the light from the above-described super-high pressure mercury lamp or from the xenon lamp, therefore, the fluophor B and G can be excited, but the fluophor R cannot be excited to a sufficient degree.

The fluophor R is often, for example, an oxide based on mixed elements of rare earth metals which is described by the general formula $(Y_{1-a-b}Gd_aEu_b)_2O_3$ (however, $0<a\leq0.90$, $0.01\leq b\leq0.20$) or a boron oxide based on mixed elements of the rare earth metals is used which is described by the general formula $(Y, Gd, Eu)BO_3$ or $(Y, Gd)BO_3$.

With respect to the excitation energy however, in any case, the situation is the same. Sufficient fluorescence cannot be obtained by the light from a super-high pressure mercury lamp or a xenon lamp.

SUMMARY OF THE INVENTION

The invention eliminates the above-described disadvantages in the prior art. The object of the invention is to enable the application state of the fluophors to be easily tested within a short time while, at the same time, enabling the application state of the fluophors to be automatically tested, by increasing the emission amount of red (R) such that it is made the same as the emission amount of green (G) and blue (B). A light with a shorter wavelength than the wavelengths of the light emitted from a super-high pressure mercury lamp or a xenon lamp is used as excitation light for sufficient excitation of the fluophor R light. When the wavelength becomes shorter, the photon energy becomes accordingly greater.

As a result of various studies, it was found that when a light source is used which emits light with a wavelength less than or equal to 230 nm, the emission amount of the fluophor R can be increased and it can then make the amounts of emission of the fluophors G and B the same. In the case of a wavelength of less than or equal to 200 nm, however, a large amount of ozone is formed. Therefore, it is difficult to use it in air and its use as a light source of a test device is not possible.

Therefore, it is desirable in testing of fluophors to use a lamp which can emit light with wavelengths from 200 to 230 nm with sufficient radiation intensity.

These lamps were studied and it was found that (1) Discharge lamp of the short-arc type in which an arc tube is filled at least with cadmium and rare gas and which has emission lines between 200 nm and 230 nm; and (2) Dielectric barrier discharge excimer lamp which has electrodes for carrying out a dielectric barrier discharge and a discharge vessel which is filled with krypton gas and chlorine gas, in which light emerges which is emitted by krypton chloride excimer molecules which have been produced by this dielectric barrier discharge, and which has emission lines between 200 nm and 230 nm.

A type (1) discharge lamp of the short-arc type is described, for example, in the Japanese patent specification 2775694 described below (JP-OS HEI 6-318449 corresponding to U.S. Pat. No. 5,481,159) and in the Japanese patent specification 3020397 described below (JP-OS HEI 7-21980 corresponding to U.S. Pat. No. 5,471,278) and the like. Such a lamp has emission spectra at a wavelength in the vicinity of 215 nm; and A type (2) dielectric barrier discharge excimer lamp is described, for example, in the Japanese patent specification 3171004 described below and the like. One such lamp has emission spectra at a wavelength in the vicinity of 222 nm. Furthermore, a dielectric barrier discharge excimer lamp is known which emits light with a wavelength of at most 200 nm. When such a lamp is used, as was described above, a large amount of ozone is formed. Therefore, such a lamp cannot be used for a test device in practice.

If, using the above-described lamps as the excitation light source, the above-described fluophors are illuminated, the fluophor R also emits with the same amount of light as G and B. In this way, it is possible to carry out the test easily, and moreover, in a short time.

Furthermore, using the above-described lamps, a test device for fluophors can be arranged in the manner described below.

The above-described type (1) or (2) lamps are used for the light source. The fluophors are irradiated with light from this light source, the fluorescence emitted from these fluophors is received by a CCD sensor or the like, it is displayed in a display device or the like and the application state, such as faults or the like of the fluophors, is checked. Furthermore, the images detected by the CCD sensor can be input to a control device and testing can be automated.

An above-described type (2) lamp that is rod-shaped is used for the light source. The light emitted from this lamp is focused by means of a trough-like focusing mirror, the fluophors are irradiated with it and the light produced by the fluophors is received by the CCD sensor. The fluophor application surfaces as test articles or the above-described dielectric barrier discharge excimer lamp are moved relative to the CCD sensor such that all fluophor application surfaces are irradiated with the light from the above-described lamp. The images received by the CCD sensor are displayed in the display device or the like and the application state, such as faults or the like of the fluophors, is tested. Furthermore, the images picked up by the CCD sensor can be input into a control device and testing can be automated.

The above-described discharge lamp of the short arc type is used for the light source. The light emitted by this lamp is focused by means of a focusing mirror, is routed through optical fibers onto the fluophor application surfaces, the fluophors are irradiated with it and the light produced by the fluophors is received by the CCD sensor. The fluophor application surfaces as the test items or the optical fibers and the CCD sensor are moved relative to one another such that all fluophor application surfaces are irradiated with light from the above-described lamp. The images picked up by the CCD sensor are displayed in the display device or the like and the application state, such as faults or the like of the fluophors, is checked. Furthermore, the images picked up by the CCD sensor can be input to a control device and testing can be automated.

By the above-described measure that the fluophor application surfaces as the test articles or the above-described lamp or the optical fibers and the CCD sensor are moved relative to one another such that all fluophor application surfaces are irradiated with light from the lamp, the test articles can be checked within a short time. In particular, by using a rod-shaped dielectric barrier discharge excimer lamp all fluophor application surfaces can be irradiated with light from the lamp by only one-time scanning and testing can be done within a short time. Furthermore, by automating the test the test duration can be shortened even more than in a visual check.

DETAILED DESCRIPTION OF THE INVENTION

Figure 1:
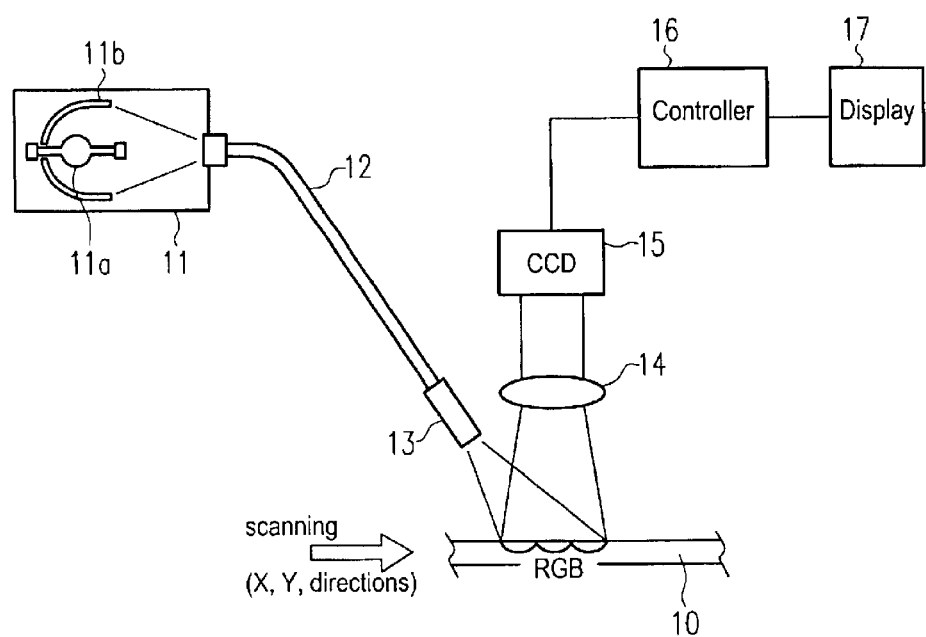
FIG. 1 shows a schematic of the arrangement of the first embodiment of the device as claimed in the invention for test fluophors.

FIG. 1 shows the arrangement of a first embodiment of the device in accordance with the invention for testing of fluophors. In this embodiment, a discharge lamp of the short arc type (hereinafter "cadmium" lamp) is used in which the arc tube is filled with a lamp filling comprising cadmium and a rare gas and which has emission lines between 200 nm to 230 nm.

FIG. 1 illustrates a light irradiation part 11 in which a cadmium lamp 11a and a focusing mirror 11b, which reflects the light from this cadmium lamp 11a, are located. The light focused by the focusing mirror 11b is routed to the vicinity of a test article 10 (here fluophors which were applied to a substrate for a display) which is being tested by optical fibers 12. At the light outlet end of the optical fibers 12 a lens unit 13 of several lenses is installed and directs the emerging light.

The light emitted onto the fluophors acts as excitation light for the fluophors. The fluophors emit fluorescent light with the respective color. The generated fluorescence is imaged by the lens 14 on the CCD sensor 15 which outputs to a controller 16 signals which correspond to the colors and the amounts of light of the generated fluorescence. The controller 16 based on these signals carries out display in a display part 17, such as in a display or the like. In the case of visual checking the test personnel watches the display part 17, and in the above-described manner, checks whether there is any outswelling, any faults, mixing or nonuniformity in the fluophors.

Figure 2A:
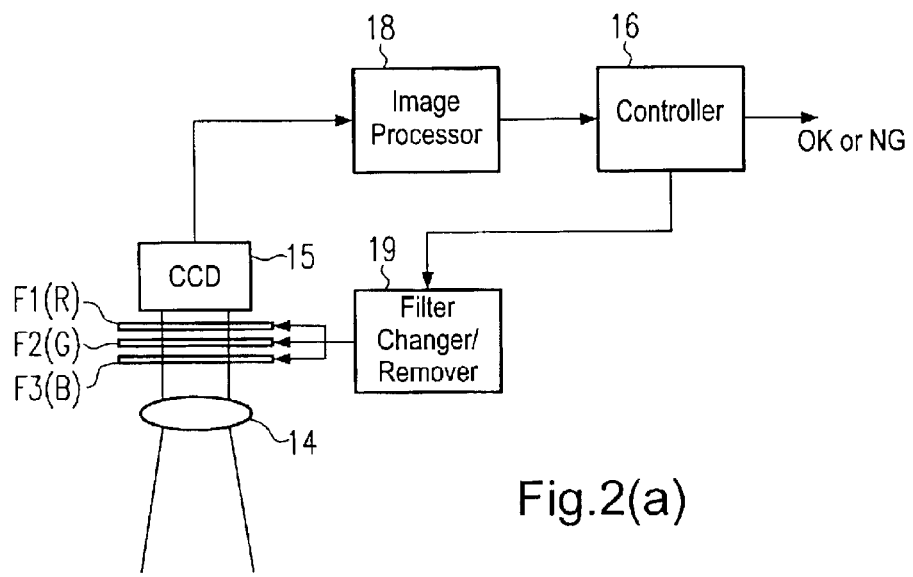
FIGS. 2(a) & 2(b) each show a schematic of an arrangement in the case of automatic testing using the test device as shown in FIG. 1.

In the case of automation of the test using a device, as shown, for example, in FIG. 2(a), in front of the CCD sensor 15 there are filters F1 to F3 of R, G, and B and a filter changing/removing means 19 by which the filters F1 to F3 of R, G, and B are switched. The images of R, G and B are each picked up by the CCD sensor 15, subjected to image processing by the image processing part 18, and input to the controller 16. Regions which are allowable with respect to the test result are input beforehand into the controller 16. The controller 16 for the images of R, G, and B checks for each whether errors, nonuniformities, or the like are located in the above-described regions, places these images on top one of another, checks whether overlaps and outswelling are within tolerance and assesses "serviceable or not serviceable" of the test article 10.

By scanning of the optical fibers 12, the lens unit 13, the above-described lens 14 and the CCD sensor 15 or by scanning the test article 10 to the right and left and/or perpendicular to the page of the drawings the image of the entire area of the test article 10 can be introduced into the CCD sensor 15.

In the case of moving the optical fibers 12, in the light irradiation part 11, there can be, for example, a X–Y movement device and thus the light irradiation part 11 and the optical fibers 12 can be moved as an integral part.

Figure 2B:
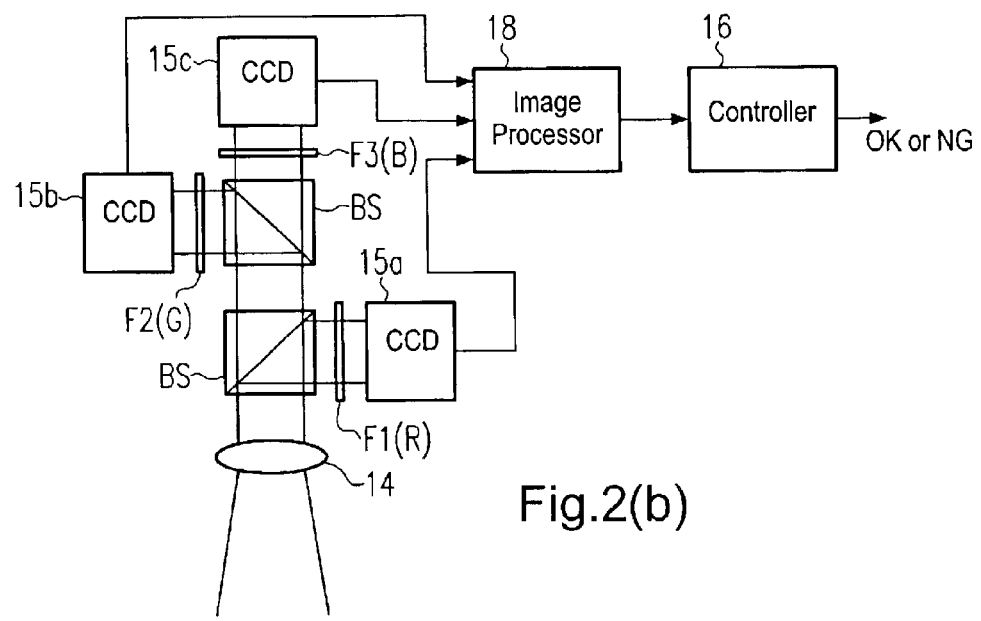

As shown in FIG. 2(b), there can be a respective filter F1 to F3 with R, G and B in front of each of three CCD sensors, the images recorded by each of the CCD sensors can each be input into the image processing part 18 by the beam splitters BS, and in the same manner as described above it can be assessed whether "serviceable or not serviceable".

Figure 3:
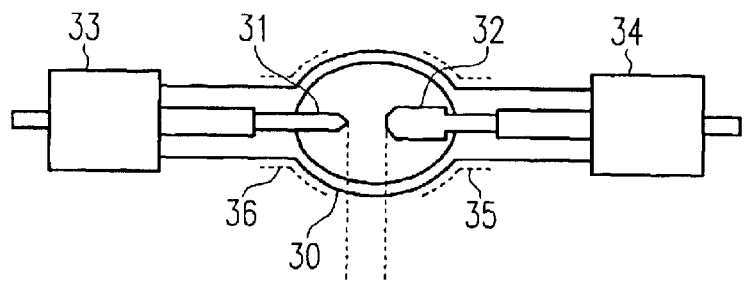
FIG. 3 shows a schematic of a sample arrangement of a cadmium lamp of the short arc type which is used in the first embodiment.

FIG. 3 shows a sample arrangement of a cadmium lamp of the short arc type which is used in this embodiment. As is shown in FIG. 3, in a silica glass arc tube 30 there are a cathode 31 and an anode 32 with a given distance to one another, and the two ends of the arc tube are provided with bases 33 and 34. The arc tube 30 is filled for example with argon and 0.3 mg/cm$^3$ metallic cadmium. The filling pressure of the argon is roughly 0.3 MPa (converted at normal temperature).

Figure 4:
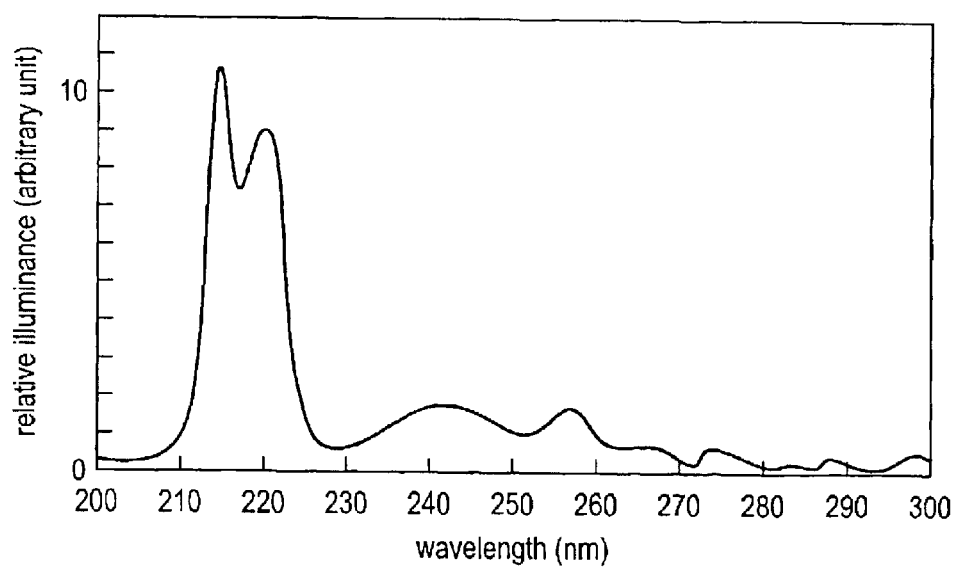
FIG. 4 shows a schematic of the spectral distribution of the cadmium lamp as shown in FIG. 3.

FIG. 4 shows the spectral distribution of the above-described cadmium lamp. In FIG. 4, the x-axis plots the wavelength (nm) and the y-axis plots the relative spectral irradiance (arbitrary unit).

As is shown in FIG. 4, the cadmium lamp with the above-described arrangement has emission lines at a wavelength in the vicinity of 215 nm. In this way, as described above, the fluophor of R can be caused to emit with the same amount of light as G and B. The cadmium lamp with the above-described arrangement at wavelengths of less than or equal to 200 nm has a small amount of light (not shown in the drawings). This prevents a large amount of ozone from being formed.

Figure 5:
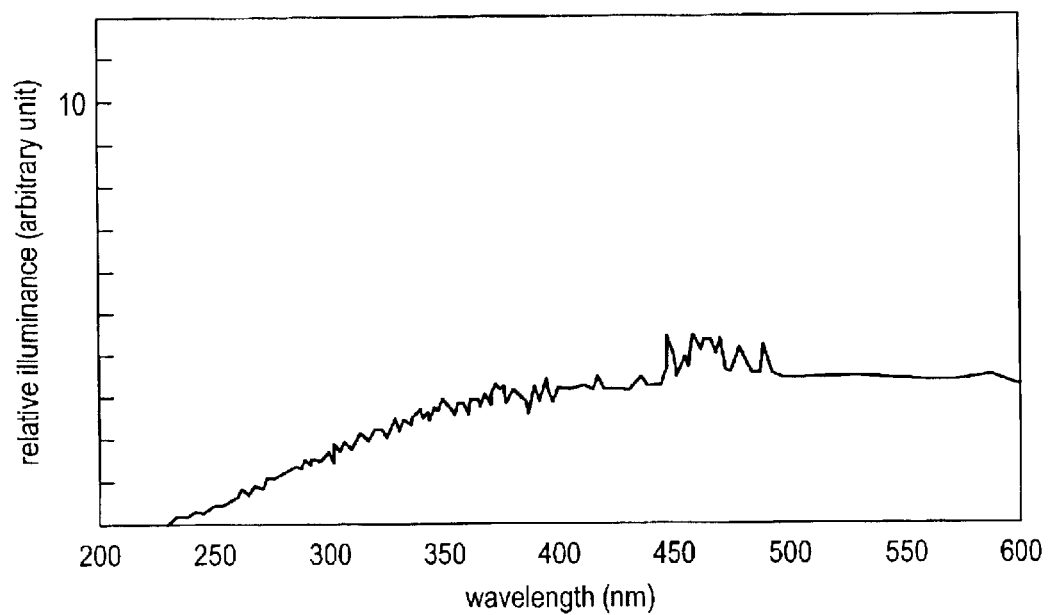
FIG. 5 shows a schematic of the spectral distribution of the xenon lamp.
Figure 6:
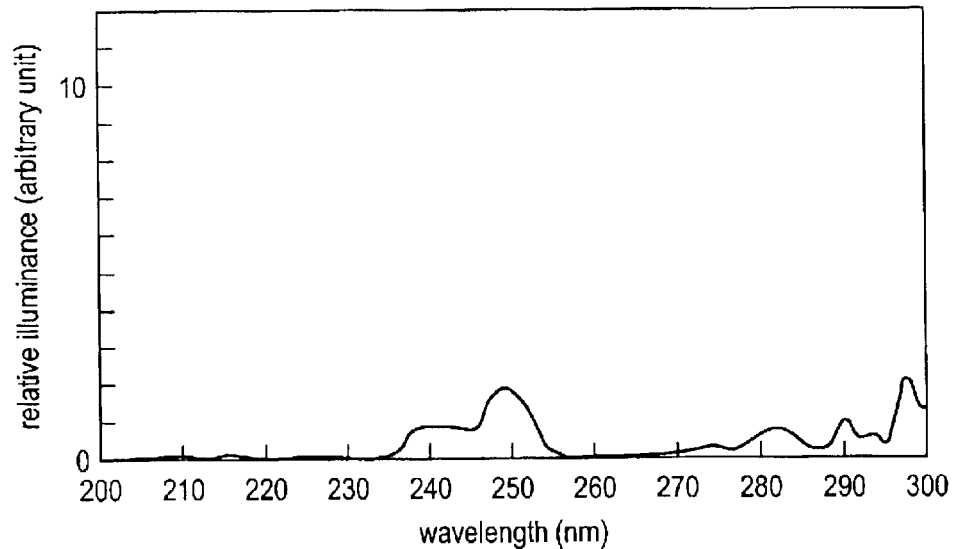
FIG. 6 shows a schematic of the spectral distribution of a super-high pressure mercury lamp.

FIGS. 5 and 6 each show the spectral distribution of the above-described xenon lamp and the above-described super-high pressure mercury lamp. In FIG. 5 and FIG. 6, the x-axis plots the wavelength (nm) and the y-axis plots the relative spectral irradiance (arbitrary unit), as in FIG. 4.

As is shown in FIG. 5 and FIG. 6, for the xenon lamp and the super-high pressure mercury lamp the relative spectral irradiance at a wavelength of roughly 200 nm to 230 nm is essentially 0. Therefore, the fluophor R cannot be excited to a sufficient degree.

The above-described cadmium lamp which has emission lines at wavelengths of roughly 200 nm to 230 nm is disclosed, for example, in the Japanese patent disclosure documents HEI 6-318449 (U.S. Pat. No. 5,481,159), HEI 7-50154 (U.S. Pat. No. 5,541,481), HEI 7-50153, HEI 7-21980 (U.S. Pat. No. 5,471,278), HEI 8-195186 (U.S. Pat. No. 5,739,636), and the like. The cadmium lamps disclosed in these publications can also be used.

In the lamp described in Japanese patent disclosure document HEI 6-318449 (U.S. Pat. No. 5,481,159), the arc tube is filled with cadmium as the main emission substance in the amount at which the partial pressure during operation is $3 \times 10^3$ Pa to $1.3 \times 10^5$ Pa.

In the lamps described in Japanese patent disclosure documents HEI 7-50154 (U.S. Pat. No. 5,541,481) and HEI 7-21980 (U.S. Pat. No. 5,471,278), the arc tube is filled with metallic cadmium in the range in which the pressure during steady-state operation is 14 kPa to 200 kPa.

In the lamp described in Japanese patent disclosure document HEI 7-50153 the arc tube is filled with cadmium in the amount in which the cadmium completely vaporizes in steady-state operation.

In the lamp described in Japanese patent disclosure documents HEI 7-195186 (U.S. Pat. No. 5,739,636) the arc tube is filled with metallic cadmium in the range in which the pressure during steady-state operation is 2 kPa to 200 kPa. By using these lamps, as in the above-described case, light can be emitted which has emission lines between 200 nm and 230 nm.

A deuterium lamp is known as the lamp which emits light with a shorter wavelength than a xenon lamp. In the case of a deuterium lamp however the amount of light is small. Emissions of the fluophors are also low. Only a dark emission can be obtained, as in a conventional case.

A second embodiment of the invention is described below. In this embodiment, a rod-shaped dielectric barrier discharge excimer lamp is used as the lamp which has emission lines between 200 nm and 230 nm.

Figure 7:
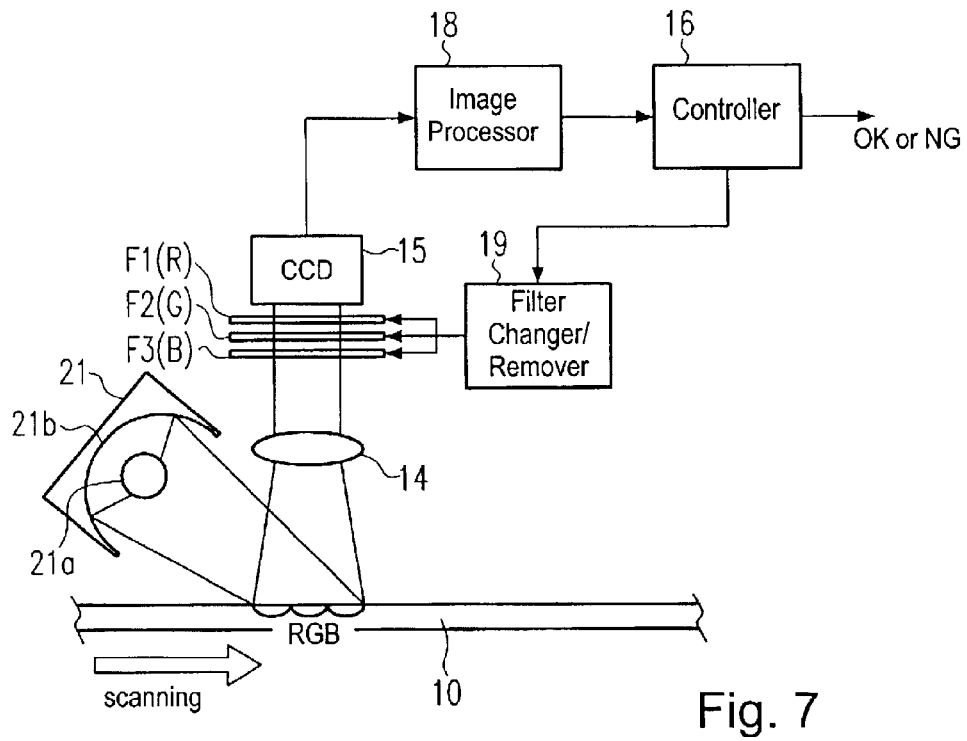
FIG. 7 shows a schematic of the arrangement of a second embodiment of the device in accordance with the invention for testing of fluophors.

FIG. 7 shows the arrangement of a device for testing fluophors in this embodiment. FIG. 7 is a cross section of a dielectric barrier discharge lamp in the direction perpendicular to the tube axis. In FIG. 7, in the light irradiation part 21 there are a rod-shaped dielectric barrier discharge excimer lamp 21a and a trough-like mirror 21b which reflects the light of this lamp 21a in the direction to the test article 10 (here fluophors which have been applied to the substrate for image display). The length of the dielectric barrier discharge excimer lamp 21a in the direction perpendicular to the page of the drawings as shown in FIG. 7 is greater than the length of the test article 10 in the direction perpendicular to the page of the drawings as shown in FIG. 7.

The light which has been emitted from the dielectric barrier discharge excimer lamp 21a and with which the fluophors of the test article 10 are irradiated acts as excitation light for the fluophors. The fluophors emit fluorescence of the respective color. The emitted fluorescence is imaged onto the CCD sensor 15 by the lens 14.

In front of the CCD sensor 15, there are filters F1 to F3 of R, G, and B and a filter changing/removing means 19 and the images of R, G, and B are each received by the CCD sensor 15.

A line sensor is used as the CCD sensor 15 and it is as long as or longer than the test article 10 in the direction perpendicular to the page of the drawings as shown in FIG. 7. By scanning the above-described light irradiation part 21, the above-described lens 14 and the CCD sensor 15 or by scanning the test article 10 to the right and left in the page of the drawings, images of the entire surface of the test article 10 can be delivered to the CCD sensor 15 by only one-time scanning.

In front of the CCD sensor 15, there are filters F1 to F3 of R, G, and B and a filter changing/removing means 19, and the filters F1 to F3 of R, G, and B, as was described above, are switched by the filter changing/removing means 19. The images of R, G, and B which were recorded by the CCD sensor 15 are each subjected to image processing by the image processing part 18 and are input into the controller 16.

The controller 16 for the images of R, G, and B checks each to determine whether faults, nonuniformities, and the like are within the above-described tolerance, places these images on top one of another, checks whether overlaps and swelling-out are within tolerance, and assesses "serviceable or not serviceable" of the test article, as was described above.

As was shown above using FIG. 2(*b*), in front of the three CCD sensors there can be filters F1 to F3 with R, G, and B, the images recorded by each of the CCD sensors can be input into the image processing part 18 by the beam splitters BS or the like and it can be assessed in the same way as the described above whether it is "serviceable or unserviceable". In the case of a visual check, as was described above, in a display part the images are displayed and the test personnel checks whether there is any outswelling, faults, mixing or nonuniformity or the like in the fluophors.

For example, the lamp disclosed in Japanese patent specification 3171004 in FIG. 1 can be used as the dielectric barrier discharge lamp 21a.

Figure 8:
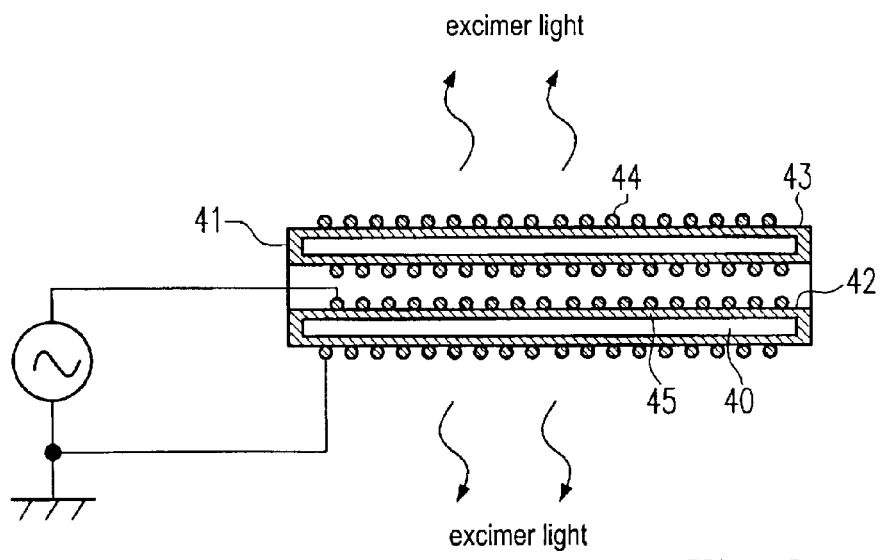
FIG. 8 shows a schematic of one sample arrangement of a dielectric barrier discharge excimer lamp which is used in the second embodiment.

FIG. 8 shows an example of the arrangement of the above-described dielectric barrier discharge excimer lamp. In FIG. 8, the discharge vessel 41 is made of silica glass, and is formed to be hollow-cylindrical by the coaxial arrangement of an inner tube 42 and an outer tube 43 to one another. The inner tube 42 and the outer tube 43 also act as a dielectric of the dielectric barrier discharge and consist of silica glass with an OH radical concentration of less than or equal to 5 ppm. The outside of the inner tube 42 is provided with an electrode 45 and the outside of the outer tube 43 is provided with an electrode 44. The electrodes 44, 45 are made of a metal net which transmits light.

The discharge space 40 is filled with krypton gas and chlorine gas as the discharge gas. The pressure of the added gas is, for example, at least 13.3 kPa and no more than 133 kPa. The chlorine concentration is at least 0.1% by volume and no more than 2% by volume with respect to krypton. The electrode 45 can also be formed from an aluminum layer which has been formed by vacuum evaporation. The aluminum layer reflects the UV radiation which is emitted by the excimer molecules of krypton with high efficiency.

Figure 9:
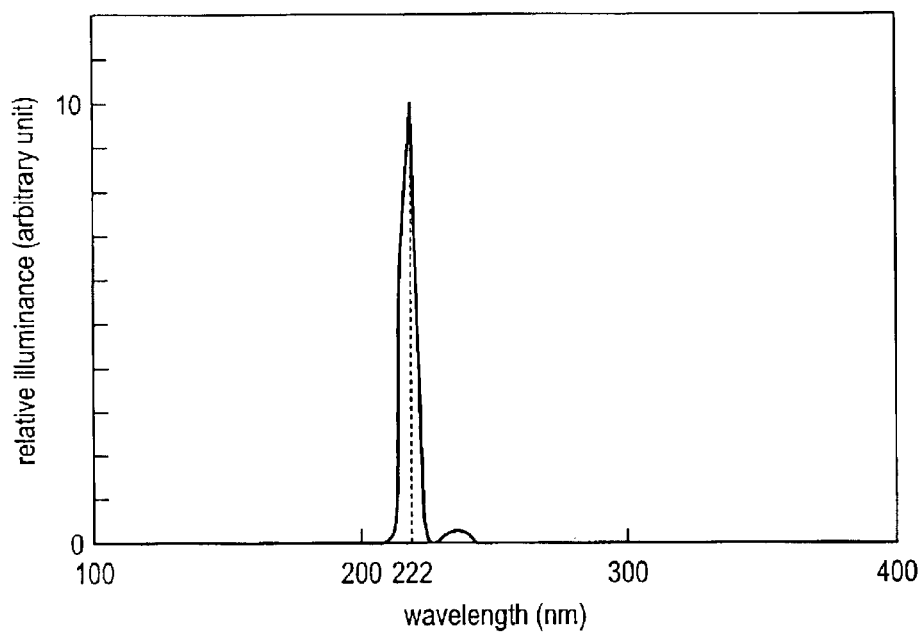
FIG. 9 shows a schematic of the spectral distribution of the dielectric barrier discharge excimer lamp shown in FIG. 8.

FIG. 9 shows the spectral distribution of the above-described dielectric barrier discharge excimer lamp. In FIG. 9, the x-axis plots the wavelength (nm) and the y-axis plot the relative spectral irradiance (arbitrary unit).

As shown in FIG. 9, the dielectric barrier discharge excimer lamp with the above-described arrangement has emission lines at the wavelength in the vicinity of 222 nm. In this way, as described above, the fluophor of R can be excited with the same amount of light as G and B. The dielectric barrier discharge excimer lamp with the above-described arrangement at wavelengths of less than or equal to 200 nm has a small amount of light, as shown in FIG. 9. Therefore a large amount of ozone is prevented from being formed.

In this embodiment, as was described above, a rod-shaped dielectric barrier discharge excimer lamp is used, a light irradiation part 21, a lens 14, a CCD sensor 15 and the test article 10 are scanned and the light emitted from the dielectric barrier discharge excimer lamp is emitted onto the overall surface of the test article. Therefore, the images of the entire surface of the test article 10 can be delivered to the image processing part 18 by only one-time scanning and thus the test article can be checked within a short time. In particular, automation of the testing makes it possible to shorten the test duration more than in visual checking.

In the above-described embodiment, a case of using a rod-shaped dielectric barrier discharge excimer lamp is described. But a dielectric barrier discharge excimer lamp of the "head-on" type disclosed in patent specification JP 3171004 B2 can also be used.

Figure 10:
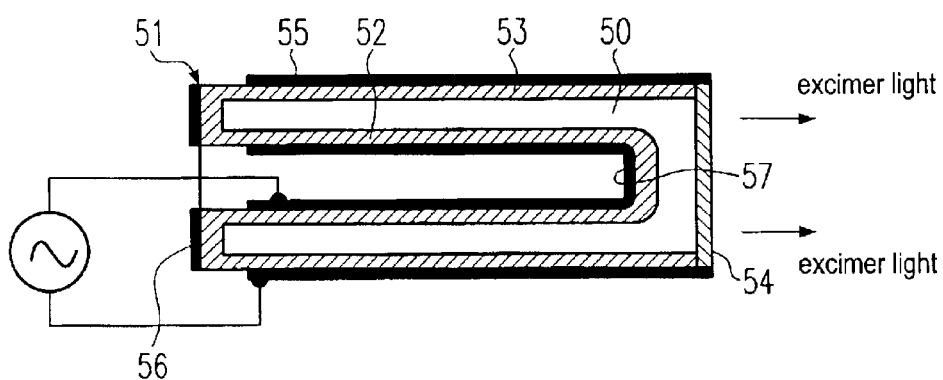
FIG. 10 shows a schematic of a sample arrangement of a dielectric barrier discharge excimer lamp of the "head-on" type.

FIG. 10 shows an example of the arrangement of the above-described dielectric barrier discharge excimer lamp of the "head-on" type. In FIG. 10, the discharge vessel 51 is made of silica glass, in which an inner tube 52 and an outer tube 53 are arranged coaxially to one another, and which forms a hollow-cylindrical discharge space 50. The inner tube 52 and the outer tube 53 also act as a dielectric of the dielectric barrier discharge and consist of silica glass with an OH radical concentration of less than or equal to 5 ppm.

On one end of the outer tube 53, a light exit window component 54 is placed by welding; it is made of a silica glass disk with an OH radical concentration of at most 700 ppm. Since the light exit window component 54 is not exposed directly to a discharge, its OH radical concentration can be higher than that of the tube material.

On the other end on which the inner tube 52 and the outer tube 53 are hermetically sealed, there is a light reflection plate 56. By vacuum evaporation of aluminum on the outside of the outer tube 53, there results an electrode 55 which acts also as a light reflection plate. Electrode 55 extends until it comes into contact with the light exit window component 54. Electrode 57 is formed by vacuum evaporation of aluminum onto the outside of the inner tube 52, i.e., the side which is opposite the side forming the inner wall of the discharge space 50. Electrode 57 also acts as a light reflection plate.

The discharge space 50 of the discharge vessel 51, as in the lamp shown in FIG. 8, is filled with krypton gas and chlorine gas as the discharge gas. The pressure of the added gas is, for example, at least 13.3 kPa and no more than 133 kPa. The chlorine concentration is at least 0.1% by volume and no more than 2% by volume with respect to krypton.

The spectral distribution of the dielectric barrier discharge excimer lamp shown in FIG. 10 is identical to that in FIG. 9 and has emission lines at a wavelength of roughly 222 nm. In this way, for the same amount of light as G and B the fluophor R can be excited to emission, as was described above.

Figure 11:
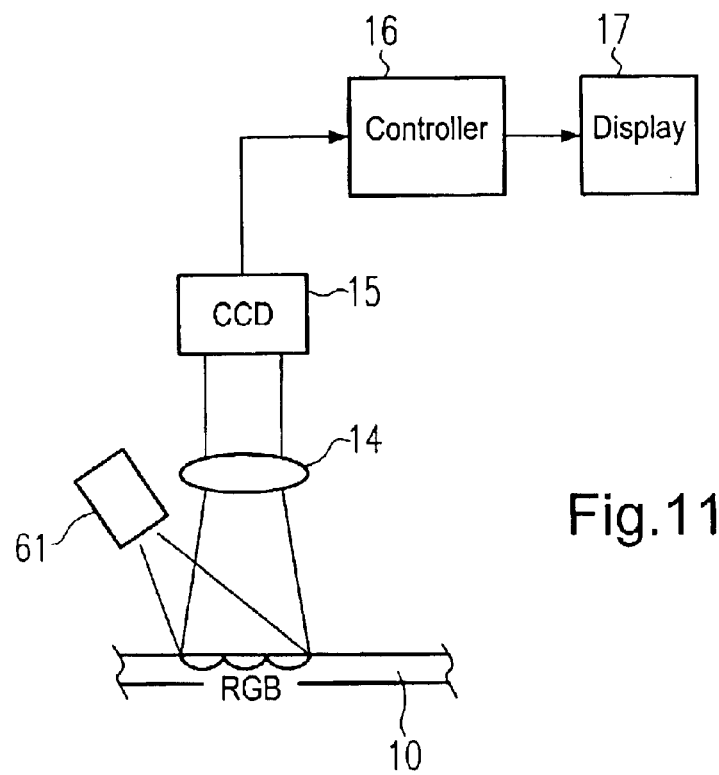
FIG. 11 shows a schematic of a sample arrangement of a test device using a dielectric barrier discharge excimer lamp of the "head-on" type.
Figure 12A:
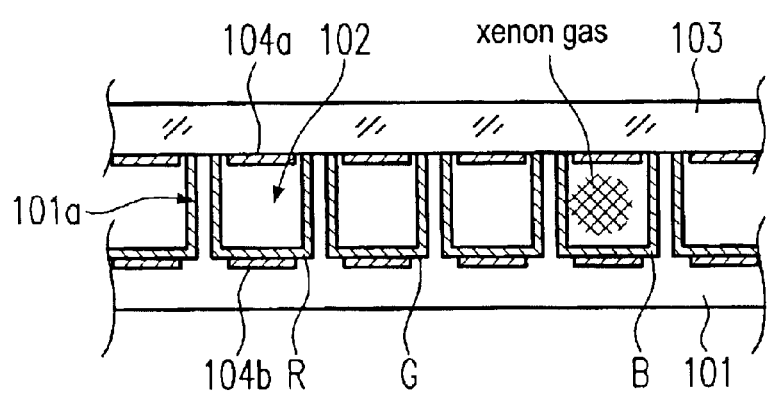
FIGS. 12(a) and 12(b) each show a schematic cross section of PDP and a schematic of testing of fluophors on the substrate.
Figure 12B:
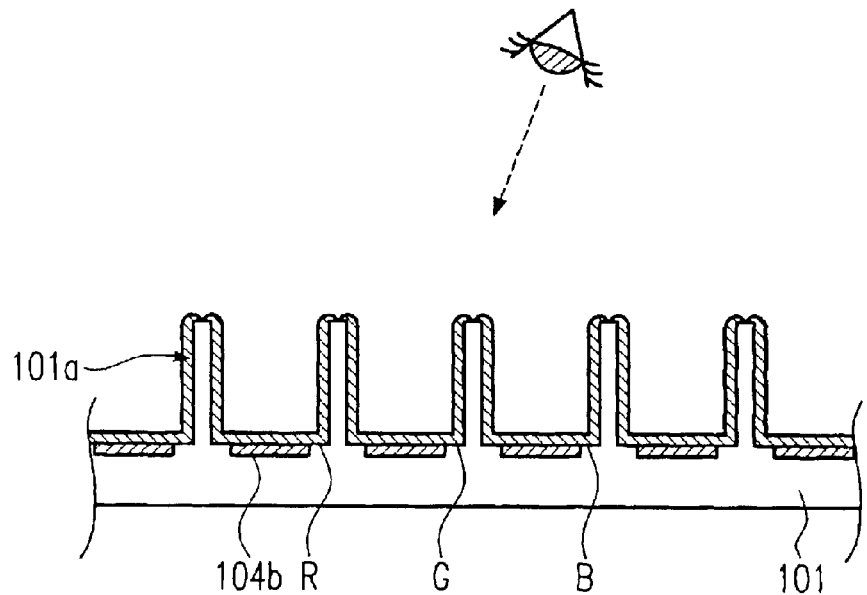
Figure 13:
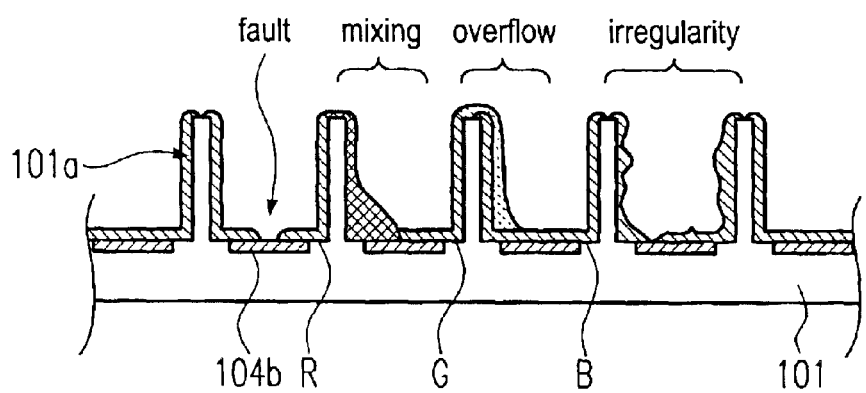
FIG. 13 shows a schematic of the criteria for testing of fluophors.

FIG. 11 shows an example of the arrangement of the test device in the case of using the above-described dielectric barrier discharge excimer lamp of the "head-on" type. The arrangement of the test device is identical to that in FIG. 1.

In FIG. 11, the cadmium lamp 11a, the focusing mirror 11b and the optical fibers 12 are replaced as shown in FIG. 1 by a dielectric barrier discharge excimer lamp of the "head-on" type 61.

The light radiated by the dielectric barrier discharge excimer lamp of the "head-on" type 61 is radiated onto the fluophors of the test article 10, as was described above. The light radiated onto the fluophors acts as excitation light for the fluophors and the fluophors emit fluorescent light of the respective color.

The generated fluorescence is, as was described above, imaged by the lens 14 onto a CCD sensor 15 which outputs signals to a controller 16, which signals correspond to the colors and the amounts of light of the fluorescence generated. The controller 16 based on these signals carries out display in a display part 17, such as in a display. In the case of visual checking the test personnel watches the display part 17 and checks in the above-described manner whether there is any outswelling, any faults, mixing or nonuniformity in the fluophors. Furthermore, as was described above, testing can also be automated.

In summary, the following effects can be obtained in accordance with the invention:

(1) By using light which is emitted by a discharge lamp of the short arc type, in which the arc tube is filled with cadmium and rare gas, and which has emission lines between 200 nm and 230 nm, or by using light which is emitted by a dielectric barrier discharge excimer lamp, which has electrodes for carrying out a dielectric barrier discharge and a discharge vessel which is filled with krypton gas and chlorine gas, in which light emerges which is radiated by the krypton chloride excimer molecules which have been produced by the dielectric barrier discharge and which has emission lines between 200 nm and 230 nm, as light for exciting the fluophors and by the fluophors thus being checked, not only green (G) and blue (B), but also the fluophor red (R) can be emitted essentially with the same amount of light as green (G) and blue (B) (roughly ½ as much to twice as much as the fluorescence emission intensity of green (G) and blue (B)). Therefore, a mixture of R with other colors and outswelling can be easily differentiated and the test time shortened; and (2) Since red (R), green (G) and blue (B) are emitted with the same amount of light, the respective emission can be picked up by a CCD sensor and the like. Automated testing using an image processing device or the like is therefore enabled.

The test article can be tested within a short time by the measure that the above-described lamp is a discharge lamp of the short arc type, in which the arc tube is filled at least with cadmium and a rare gas, and which has emission lines between 200 nm and 230 nm, or a rod-shaped dielectric barrier discharge excimer lamp is used, and that the surfaces to which the fluophors have been applied, as the test article, or the optical fibers which guide the light from the above-described discharge lamp of the short arc type, or the above-described dielectric barrier discharge excimer lamp and the CCD sensor are moved relative to one another such that the light from the discharge lamp of the short arc type in which the arc tube is filled at least with cadmium and rare gas, and which has emission lines between 200 nm and 230 nm, or the light from the dielectric barrier discharge excimer lamp is radiated onto the entire surfaces to which the fluophors have been applied. In particular, the test duration can be shortened more by automating the test than in visual checking.

What is claimed is:

1. A process for testing of fluophors comprising the steps of:
   irradiating fluophors with light to emit fluorescence;
   testing the fluophors with the emitted fluorescence; and
   wherein a discharge lamp of the short-arc type including an arc tube filled with at least one of cadmium and are gas is used as a source of said light, and wherein light with a wavelength of between 200 nm and 300 nm is used for said irradiating of the fluophors and
   wherein said fluophors are red, green and blue fluophors applied on an inner side of a cell of a substrate for image display.

2. A process for testing of fluophors comprising the steps of:
   irradiating fluophors with light to emit fluorescence;
   testing the fluophors with the emitted fluorescence; and
   wherein a dielectric barrier discharge excimer lamp comprising electrodes for carrying out a dielectric barrier discharge and a discharge vessel filled with at least krypton gas and chlorine gas, is use as a source of said light, wherein said light is emitted by krypton chloride excimer molecules produced by said dielectric barrier discharge, and wherein light with a wavelength of between 200 nm and 230 nm is used for said irradiating of the fluophors; and
   wherein said fluophors arc red, green and blue fluophors applied on an inner side of a cell of a substrate for image display.

3. A process for testing fluophors comprising the steps of:
   irradiating red, green and blue fluophors applied on an inner side of a cell of a substrate for image display to emit fluorescence using light of a wavelength between 200 nm and 230 nm produced by a light source, wherein the light source is a discharge lamp of the short-arc type in which the arc tube is filled at least with cadmium and rare gas;
   observing the fluorescence produced by the irradiation of said fluophors and
   checking the application state of the fluophors.

4. A process for testing of fluophors comprising the steps of:
   irradiating red, green and blue fluophors applied on an inner side of a cell of a substrate for image display to emit fluorescence using a dielectric barrier discharge excimer lamp having electrodes for carrying out a dielectric barrier discharge and a discharge vessel filled with at least krypton gas and chlorine gas as a light source, said light being emitted by krypton chloride excimer molecules produced by the dielectric barrier discharge in a wavelength range of between 200 nm and 230 nm;
   observing the fluorescence produced by irradiating said fluophors; and
   checking an application state of the fluophors.

5. A device for testing of fluophors comprising:
   a discharge lamp having a discharge vessel filled with at least krypton gas and chlorine gas as a light source and being adapted to emit light in a wavelength range of between 200 nm and 230 nm by dielectric barrier discharge production of krypton chloride excimer molecules;
   a light irradiation part having a focusing mirror for reflecting the light from said discharge lamp;

optical fibers operative to route the light from said light irradiation part onto surfaces to which the fluophors have been applied;

a CCD sensor operative to pick up the fluorescence produced by the fluophors; and means for moving the surfaces to which the fluophors have been applied relative to the optical fibers and the CCD such that the light from the light irradiation part is emitted onto the surfaces to which the fluophors have been applied;

wherein said fluophors are red, green and blue fluophors applied on an inner side of a cell of a substrate for image display.

6. A device for testing of fluophors comprising:

a trough-like mirror for focusing the light which is emitted from a dielectric barrier discharge excimer lamp, wherein said lamp comprises electrodes for carrying out a dielectric barrier discharge and a discharge vessel filled at least with krypton gas and chlorine gas, wherein said light is emitted by krypton chloride excimer molecules produced by a dielectric barrier discharge, and wherein said dielectric barrier discharge lamp has an has emission between 200 nm and 230 nm;

a CCD sensor for detecting the fluorescence which is produced by the fluophors; and means for moving the surfaces to which the fluophors have been applied relative to the dielectric barrier discharge excimer lamp and the CCD sensor such that the light from the dielectric barrier discharge excimer lamp is radiated onto the entire surface to which the fluophors have been applied;

wherein said fluophors are red, green and blue fluophors applied on an inner side of a cell of a substrate for image display.

* * * * *